US007491265B1

(12) United States Patent
Johnson et al.

(10) Patent No.: US 7,491,265 B1
(45) Date of Patent: Feb. 17, 2009

(54) COVER FOR ANIMAL WASTE COLLECTION AREA

(76) Inventors: Dennis J. Johnson, 1890 Red Leaf Ct., Windom, MN (US) 56101; Matthew W. Johnson, 1890 Red Leaf Ct., Windom, MN (US) 56101

( * ) Notice: Subject to any disclaimer, the term of this patent is extended or adjusted under 35 U.S.C. 154(b) by 568 days.

(21) Appl. No.: 11/155,669

(22) Filed: Jun. 17, 2005

(51) Int. Cl.
*B01D 53/02* (2006.01)

(52) U.S. Cl. .......................... 96/121; 96/134; 55/385.2; 55/511; 119/450

(58) Field of Classification Search .................. 96/108, 96/121, 134; 55/385.2, 511, 515; 119/436, 119/447, 450; 4/498; 210/170.05, 242.1, 210/DIG. 9
See application file for complete search history.

(56) References Cited

U.S. PATENT DOCUMENTS

| | | | |
|---|---|---|---|
| 4,366,806 A * | 1/1983 | Acker .......................... 126/565 |
| 4,497,712 A * | 2/1985 | Cowling ...................... 210/691 |
| 5,400,549 A * | 3/1995 | Morgan .......................... 52/23 |
| 5,562,759 A * | 10/1996 | Morgan et al. ................. 96/155 |
| 6,099,723 A * | 8/2000 | Morris et al. .......... 210/170.03 |
| 6,136,194 A * | 10/2000 | Vogel et al. .................. 210/605 |
| 6,276,304 B1 * | 8/2001 | Tai .............................. 119/448 |
| 6,451,206 B1 * | 9/2002 | Charbonneau ......... 210/170.09 |
| 6,558,548 B2 * | 5/2003 | Svirklys et al. ............. 210/603 |
| 6,673,241 B1 * | 1/2004 | Tung et al. ................ 210/242.1 |
| 2003/0066789 A1 * | 4/2003 | Morgan et al. ............... 210/120 |
| 2004/0055952 A1 * | 3/2004 | Baumgartner et al. ....... 210/605 |

OTHER PUBLICATIONS http://www.geosynthetica.net/specifications/sewing_geotextiles. asp, "Sewing Geotextiles," geosynthetica website, no date given.
http://www.novaweld.com,Novaweld website, no date given.
"Livestock and Poultry Odor Workshop I," University of Minnesota, Dept. of Biosystems and Agricultural Eng., p. 47-60; 70-76; and 101-104 (1999).
"A Summary of Livestock Odor Research at the University of Minnesota 1995-1999," University of Minnesota, Dept. of Biosystems and Agricultural Eng. (Draft), p. A.1, A.3, A.9-A.14 (Oct. 21, 1999).
Jacobson, L. et al., "Odor Control for Animal Agriculture, "BEAU-17.1, p. B.1, B.3, B.5 and B.7, (Nov. 1998, revised Feb. 2000).
"Treatment Processes Workshop, Part I, Waste Characteristics and Odors," University of Minnesota, p. 1-8 (Feb. 1999).
"Treatment Processes Workshop, Part II, Principles of Microbiology and Biochemistry in Swine Manure Odor Production," University of Minnesota, p. 15-54 (Feb. 1999).
"Treatment Processes Workshop, Odor Control," University of Minnesota, p. 100-116 (Feb. 1999).

* cited by examiner

*Primary Examiner*—Frank M Lawrence
(74) *Attorney, Agent, or Firm*—Faegre & Benson LLP

(57) ABSTRACT

A cover member adapted to confine gaseous emissions from animal waste in a waste collection area having a base for contacting and floating on at least a portion of a surface of the animal waste and a cover with at least one surface extending from the base. The cover member can include a buoyant frame to define a generally pyramid shape. The cover includes a layer of geotextile material and can include organic filter material with the internal volume of the cover member. A plurality of cover members can be closely aligned to cover a substantial portion of the surface of the animal waste.

15 Claims, 12 Drawing Sheets

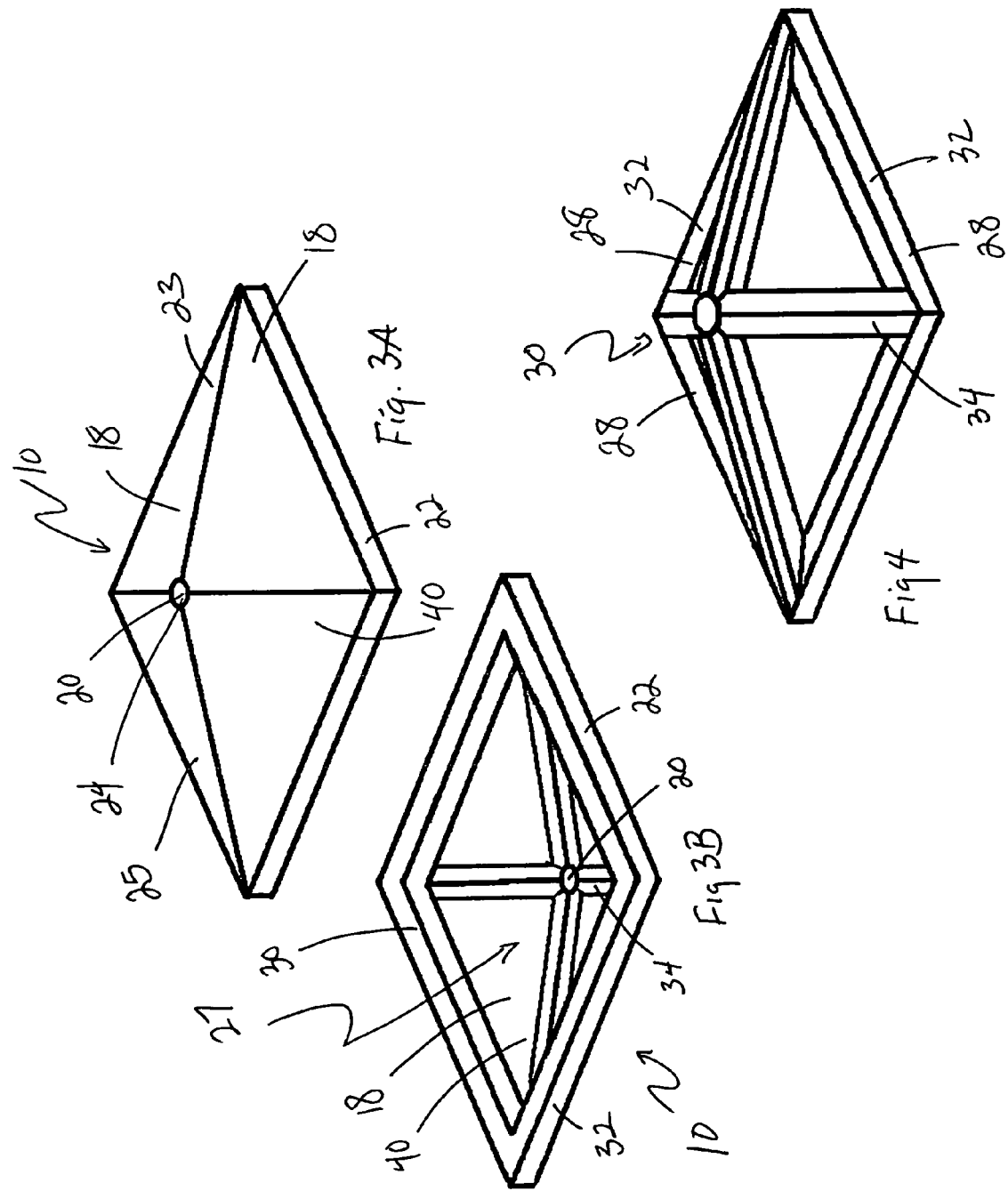

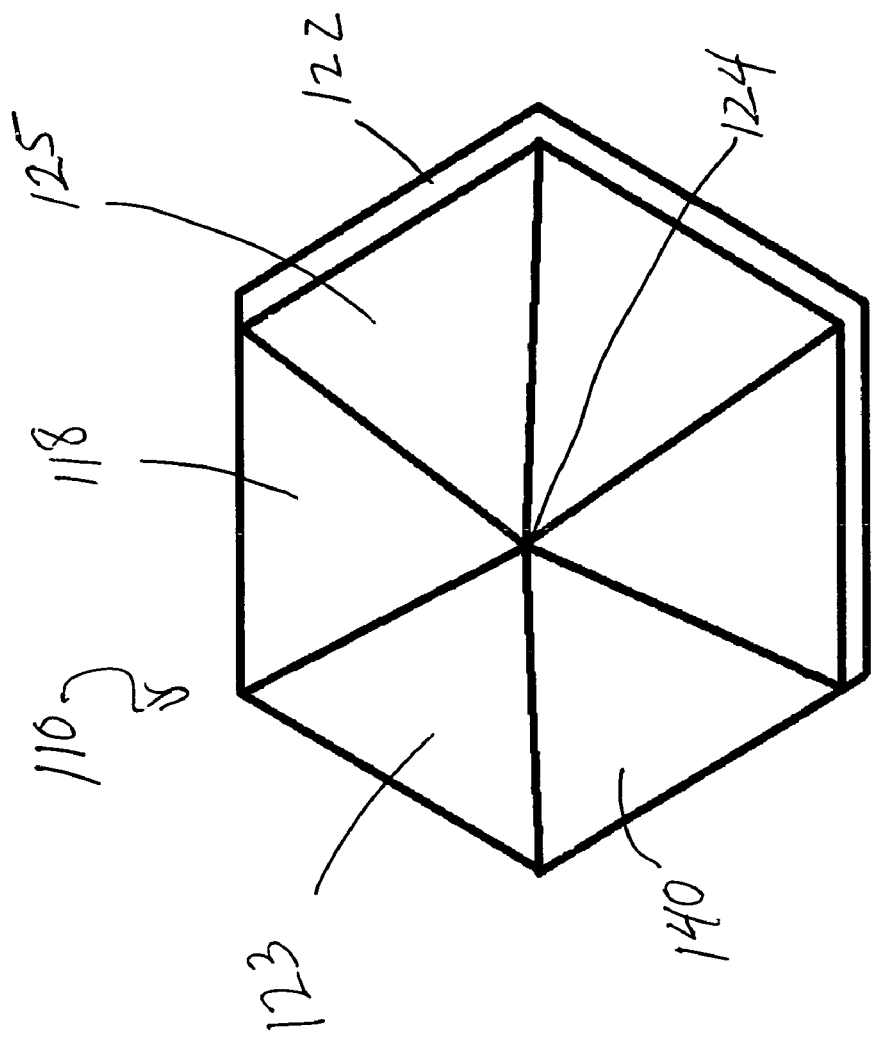

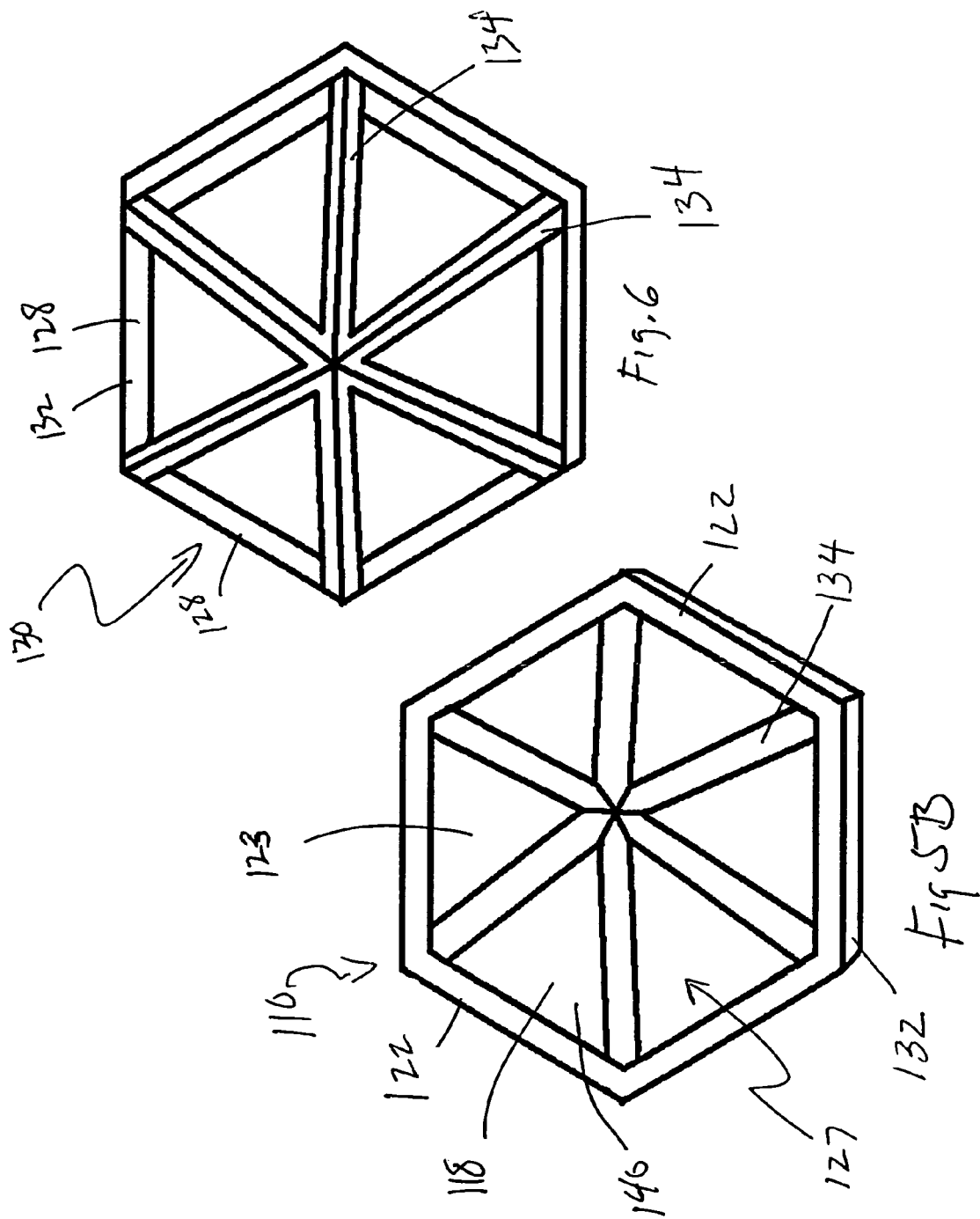

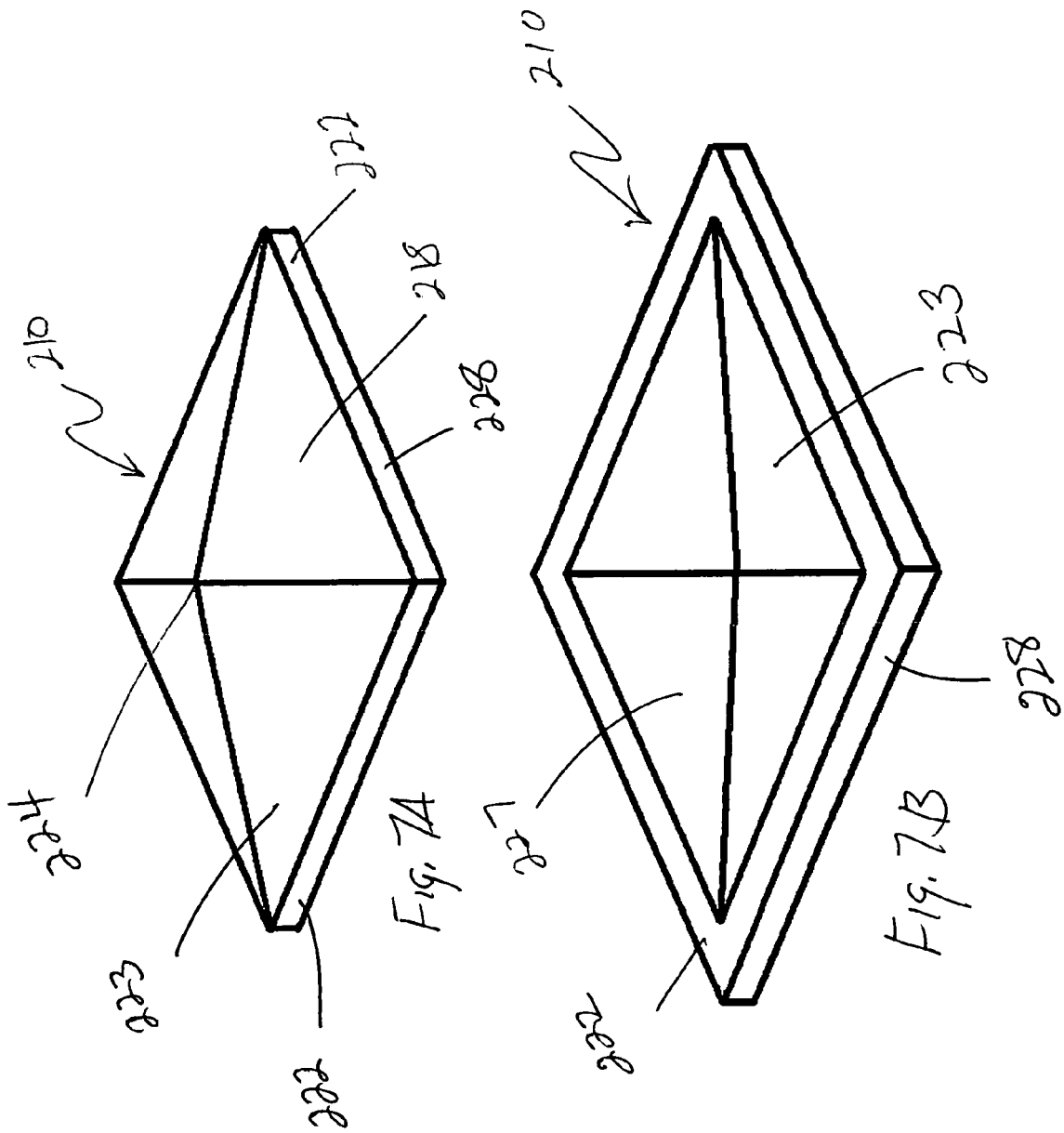

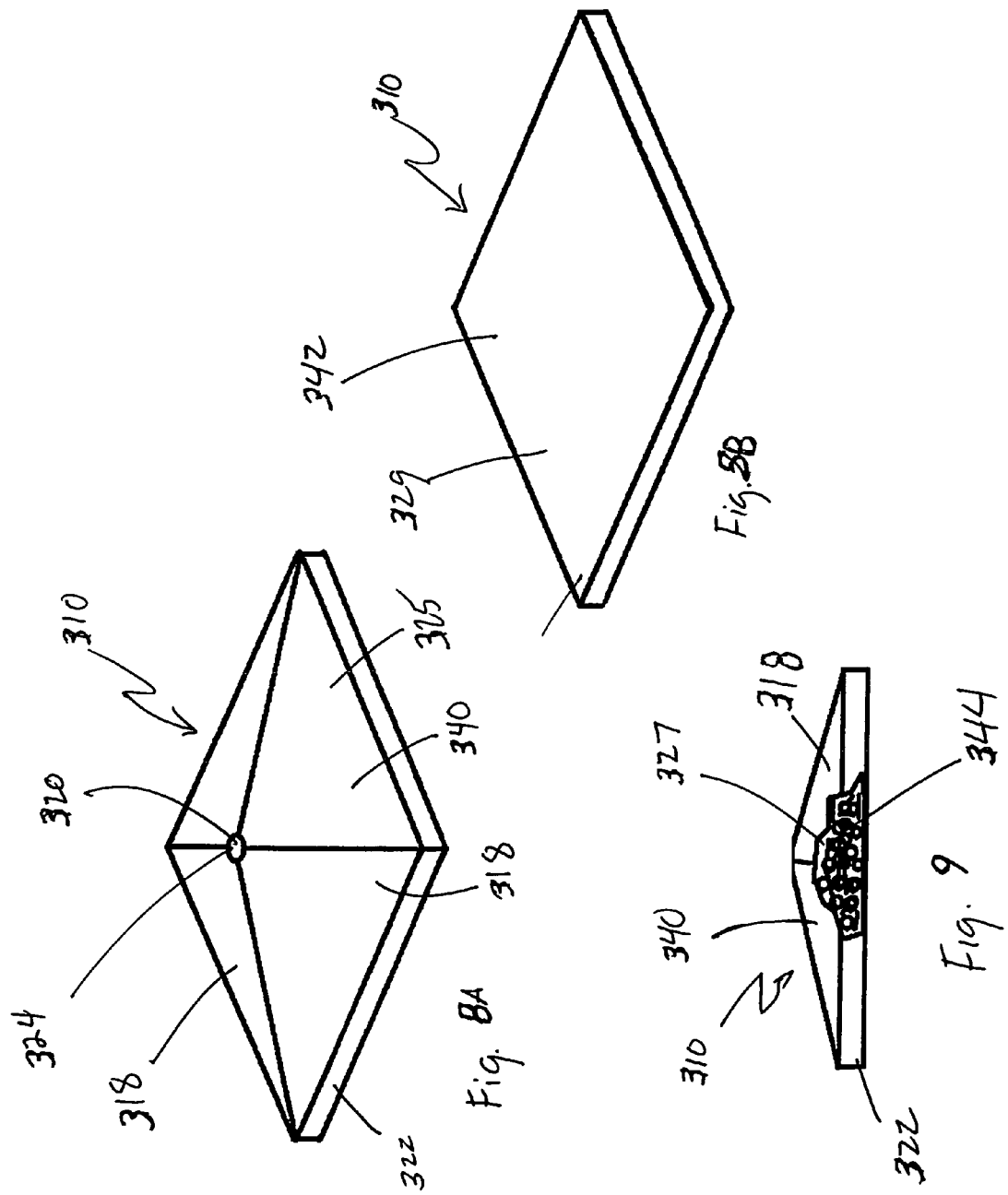

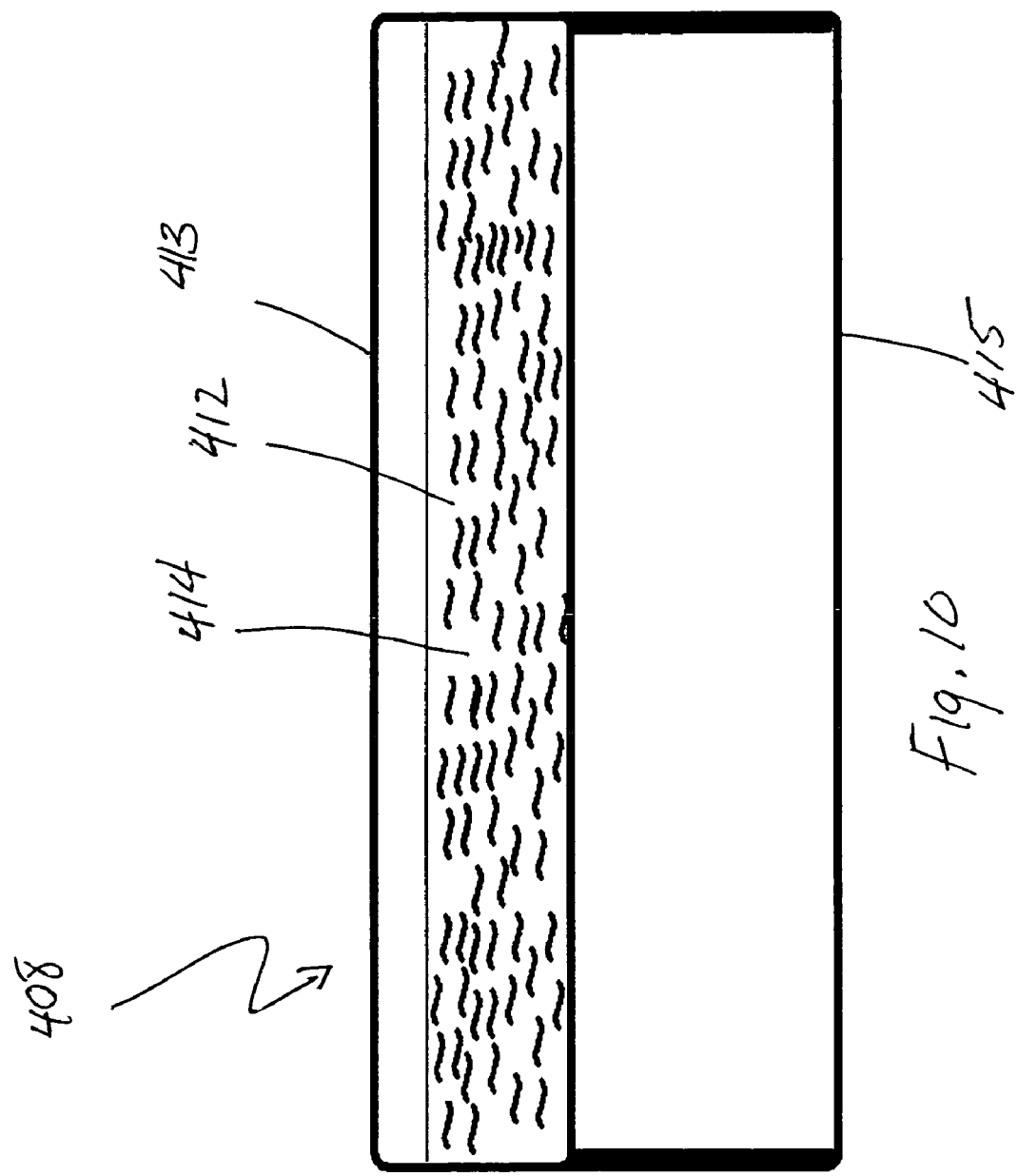

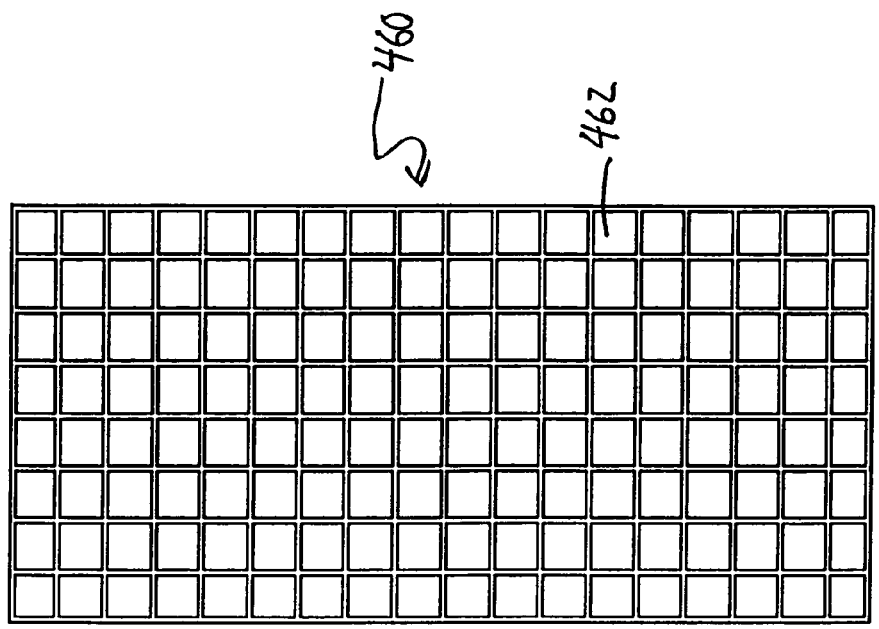
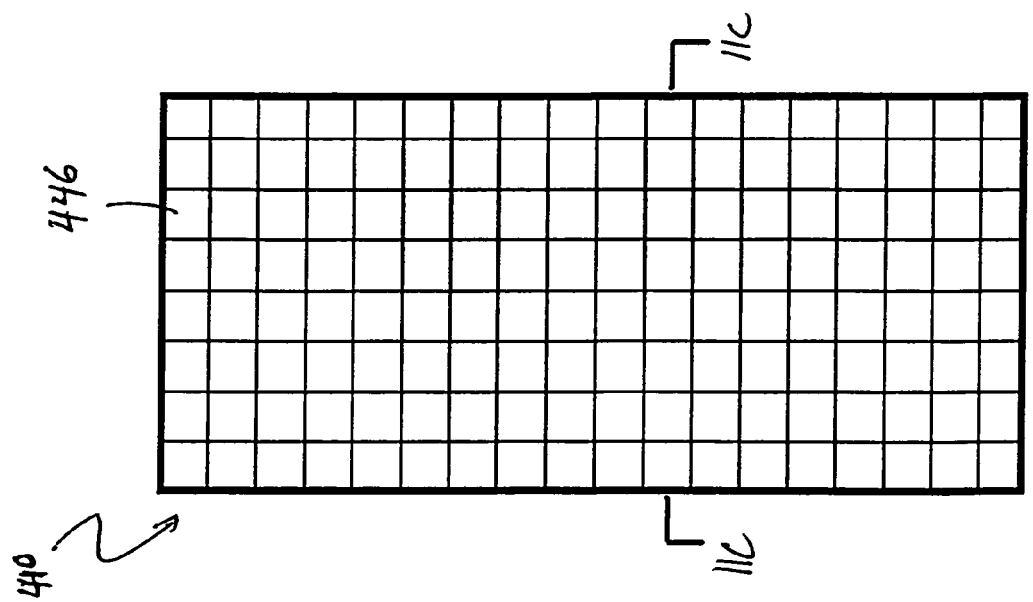

US 7,491,265 B1

COVER FOR ANIMAL WASTE COLLECTION AREA

FIELD OF THE INVENTION

The present invention relates generally to the field of odor control in agricultural applications. More particularly, the invention relates to structures for reducing or controlling emissions of odorous gases from waste collection areas including manure storage areas within an agricultural building.

BACKGROUND OF THE INVENTION

Unwanted by-products of producing livestock include the inherent odors, particularly those created by livestock waste. Livestock waste emits foul and noxious gases, including hydrogen sulfide and ammonia. Not only are these gases unpleasant and potentially dangerous for those who are located near waste collection areas, but many regulatory bodies regulate the permitted emissions of certain gases from an agricultural operation. Further, some regulatory bodies require larger agricultural operations to provide air emission plans, which include methods and practices that will be employed by the agricultural operations to minimize air emissions and procedures to respond to complaints directed at the facility, including identifying strategies to address the sources of odors and noxious gases. In addition, even if gases are somehow contained within an agricultural building or filtered through exhaust systems, the environment within the agricultural building is subjected to the foul and noxious gases, making it uncomfortable within the building for animals and humans alike. Thus, it is apparent that controlling the emission of foul odors and noxious gases is not only a desired goal, in many cases it is required by applicable regulations. What is needed, then, is an effective way to reduce the emission levels of odors and noxious gases associated with agricultural applications, including, but not limited to, emissions within farm buildings.

SUMMARY OF THE INVENTION

The invention is directed toward a cover member for an animal waste collection area having a base for contacting and floating on waste material located within the waste collection area and an upper cover portion that extends above the base to confine gaseous emissions from the waste material. The cover member has an inner volume, which can include an organic filter material. In one embodiment, the cover includes a frame and a layer of geotextile material that define an outer surface of the base and the cover. In another embodiment, the cover can include geotextile material extending across a bottom surface of its base to enclose the inner volume. One or more floating cover members can be used to cover all or part of the animal waste in the waste collection area.

The invention is also directed to a generally flat cover member having first and second layers of geotextile material that are attached to each other to form one or more pouches between the layers. The one or more pouches include an organic filtering material and buoyant materials. The cover member is adapted for contacting and floating on the surface of the animal waste to confine gaseous emissions from the animal waste.

BRIEF DESCRIPTION OF THE DRAWINGS

FIGS. 3A-B are isometric illustrations of top and bottom views of the cover member shown in FIG. 2.

FIG. 4 is an isometric view of a frame of the cover member of FIG. 2.

FIGS. 5A-B are isometric illustrations of top and bottom views, respectively, of the cover member according to another embodiment of the invention.

FIG. 6 is an isometric view of a frame of the cover member of FIGS. 5A-B.

FIGS. 7A-B are isometric illustrations of top and bottom views of the cover member according to yet another embodiment of the invention.

FIGS. 8A and 8B are isometric illustrations of top and bottom views of a cover member in accordance with yet another embodiment of the invention.

FIG. 9 is a cutaway illustration of the cover member of FIGS. 5A-B, showing filtration material located with an internal volume of the cover member.

FIG. 10 is an illustration of an alternative waste collection area located outside of an agricultural building on which a cover of the invention can be used.

FIG. 11A is an illustration of a top views of a cover member for the waste collection area of FIG. 10 in accordance with another embodiment of the invention.

FIG. 11B is a top view of a spacer adapted for use with the cover member of FIG. 1A.

DETAILED DESCRIPTION OF THE INVENTION

Figure 1:
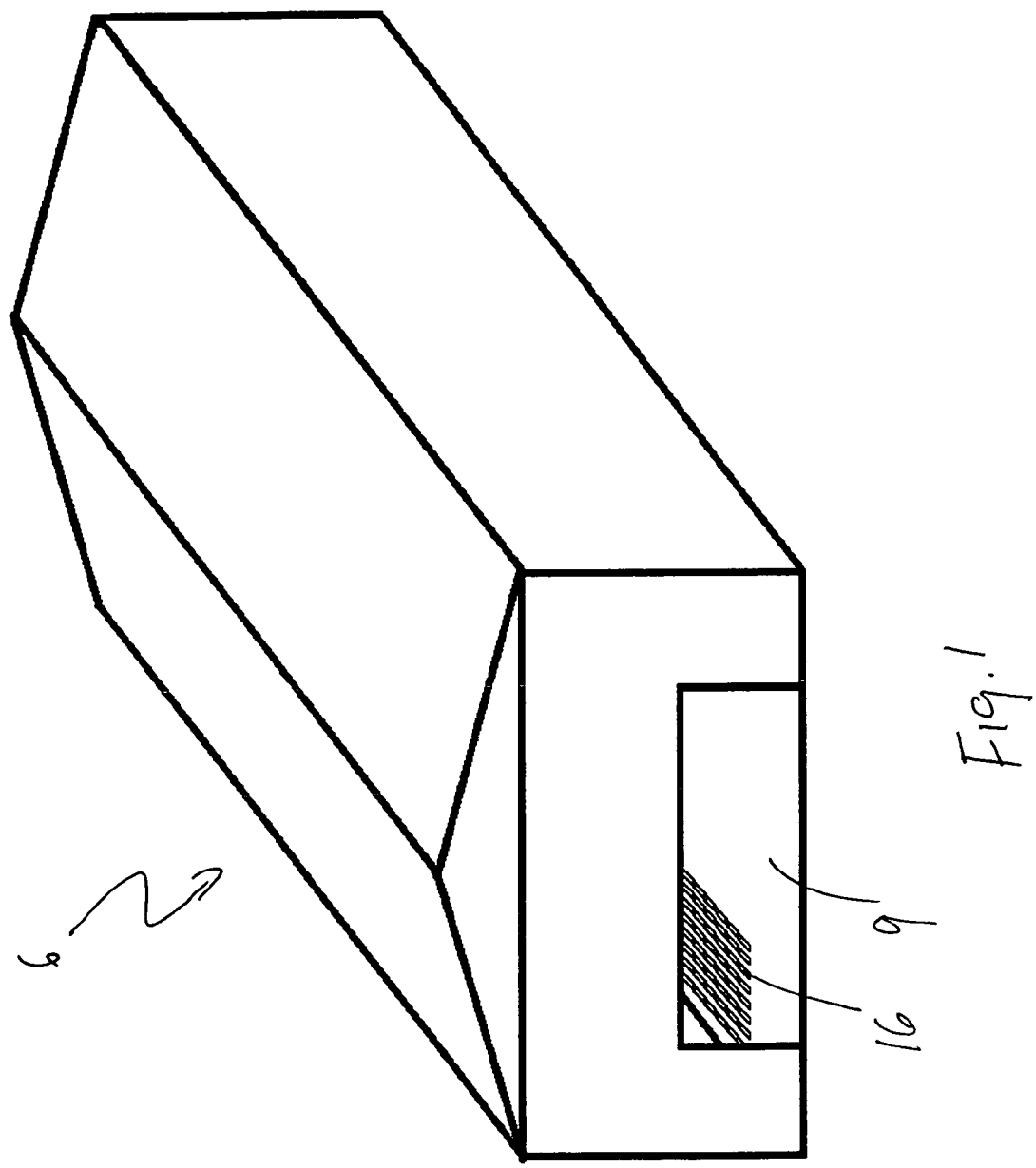
FIG. 1 is an illustration of an agricultural building having a floor with apertures to allow access to a waste collection area located beneath the floor on which a cover of the current invention can be used.
Figure 2:
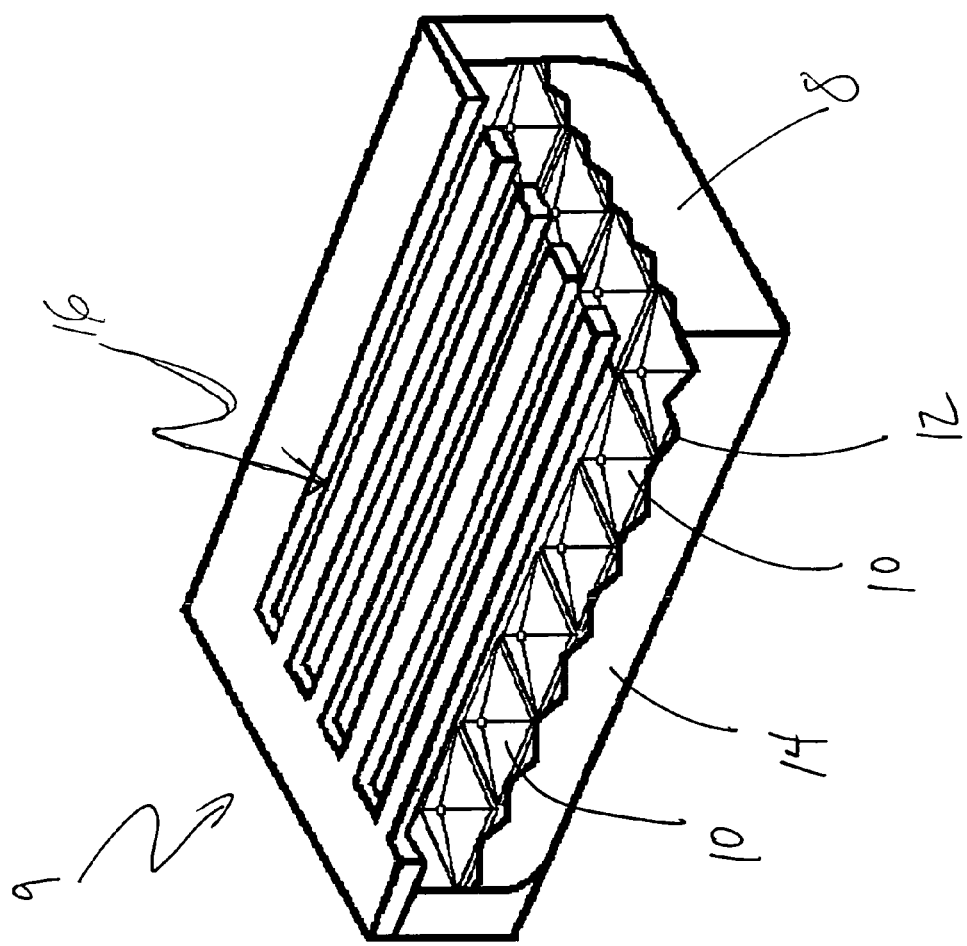
FIG. 2 illustrates a cross-sectional view of a portion of the floor in the agricultural building of FIG. 1, showing the waste collection area located beneath the apertures in the floor and a cover in accordance with one embodiment of the invention.
Figure 11C:
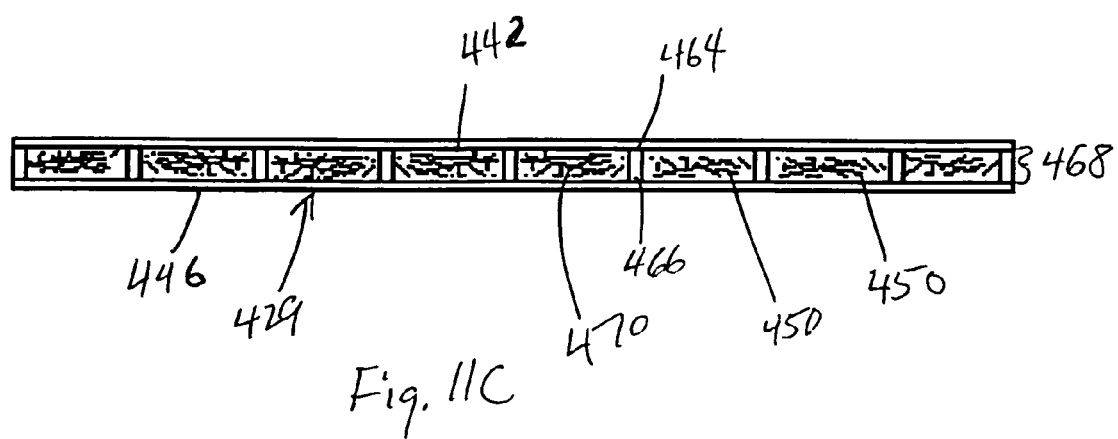
FIG. 11C is a cross-sectional view of a portion of the cover member of 11A showing first and second layers of material attached to the spacer of FIG. 11B.
Figure 12:
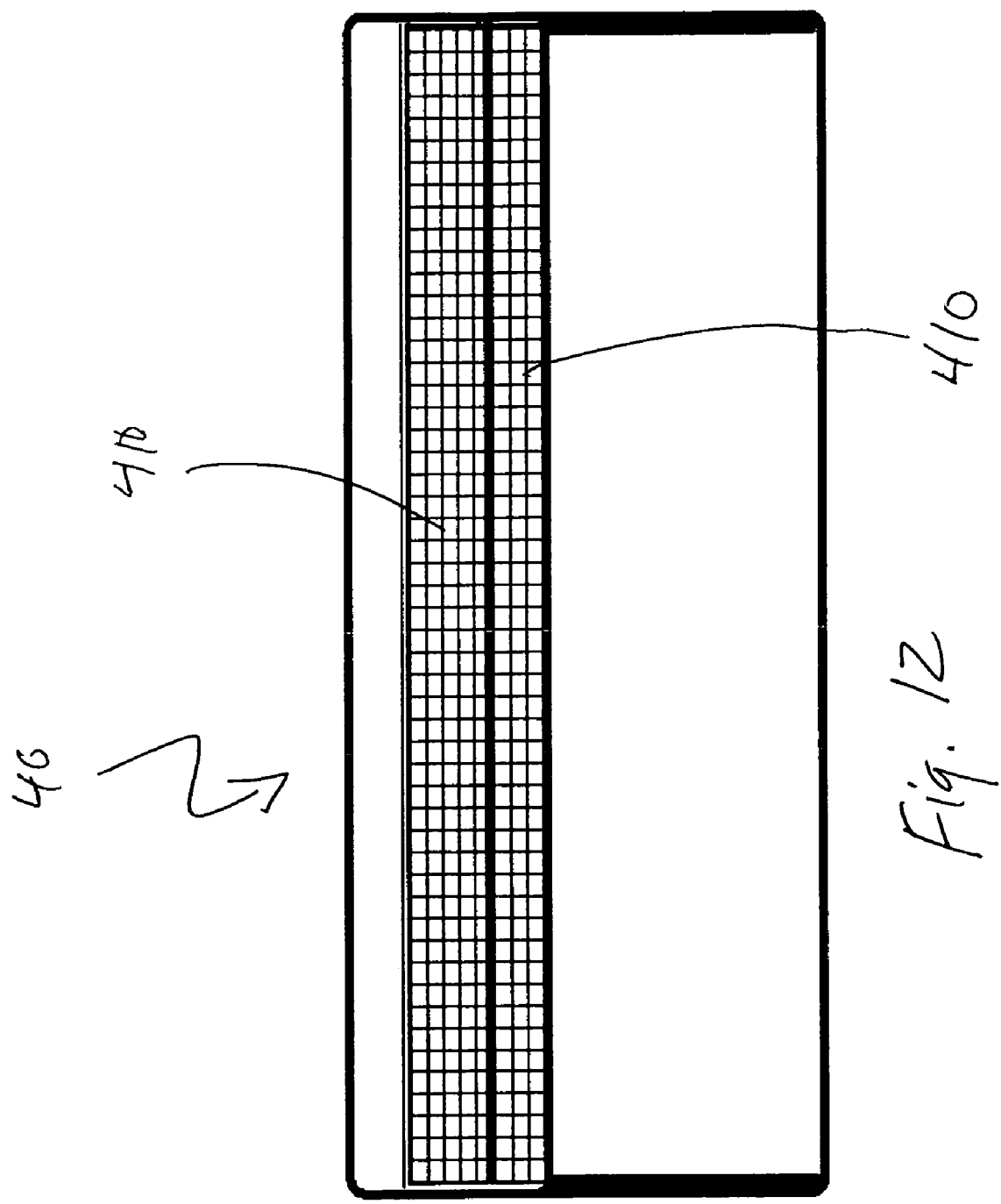
FIG. 12 is an illustration of a plurality of the cover members of FIGS. 11A and 11B positioned over the waste collection area of FIG. 10.

FIGS. 1 and 2 illustrate an agricultural building 6 having a waste collection area 8 holding waste material 14. A plurality of cover members 10 are shown floating in the waste collection area 8 according to one embodiment of the invention. Building 6 is adapted to house agricultural livestock such as hogs or other animals (not shown). At least a portion of floor 9 includes a plurality of apertures 16 formed through the floor and located over the waste collection area 8 to allow animal waste such as feces and urine to fall directly or be washed or shoveled into the waste collection area. The waste material 14 includes animal waste as well as water and various other materials that may fall or be introduced into the waste collection area. The waste material 14 typically has a generally liquid consistency and the cover members 10 float on a surface 12 of the waste material.

Cover members 10 in one embodiment, as illustrated in FIGS. 3A, 3B, and 4, have a base 22 and an upper cover portion 23 extending from the base and having a generally pyramid shape. The upper cover portion 23 has triangularly shaped and sloping lateral faces 18 extending from each side of the base toward an apex or vertex 24. The lateral faces 18 collectively define an outer surface 25 of the cover member 10. In addition, the lateral faces 18 define an inner volume 27 of the cover member. As shown in FIG. 3B, cover member 10, in one embodiment, is generally hollow, allowing for gases to accumulate within the inner volume 27 when the cover member is positioned on the waste material 14 so that the apex 24 extends above the waste material. Further, the cover member 10, in one embodiment, has an aperture 20 located near the apex 24. The aperture 20 provides a pathway from inner volume 27 through the cover member 10 to allow a small amount of gas to escape from the inner volume. Alternatively, the cover member 10 can be made without the aperture.

The cover member 10, in one embodiment, includes a frame 30 that defines the shape of the cover member 10 and a outer layer 40 of material which is attached to the frame to defined the lateral faces 18. At least a portion of frame 30 is preferably made of buoyant material, such as polyethylene, polystyrene, or other similar materials, to allow the cover member to float on waste material 14. Alternatively, buoyant material can be attached to a frame that does not have sufficient buoyancy.

The frame 30 includes a series of base segments 32 that are extend along each side 28 of the base 22 and are attached to each other at ends of the base segments to define the shape of the base. In addition, side segments 34 are attached to and extend angularly from the ends of each base segment 32 toward the apex 24 of the cover member 10, where the side segments are attached to each other. The combination of one base segment 32 and the side segments 34 extending from each end of the base segment 32 define one lateral face 18. The base segments 32 and side segments 34 can be separately manufactured and attached to each other by known processes such as by the use of fasteners or adhesive. Alternatively, the frame 30 may be formed as an integral one-piece member by utilizing injection molding, blow molding, or other known processes. In one embodiment, the base 22 has four sides 28 with a lateral face 18 extending up from each side toward the apex 24 to define a pyramid with four lateral faces 18. Alternatively, the cover member 10 may have a base 22 with a different number of sides 28 and lateral faces 18 extending from each side.

The outer layer 40, in one embodiment, includes geotextile material and is attached to the frame 30 by stapling, gluing, heat bonding or any other acceptable process. Geotextile material is a somewhat porous material, but it also acts as a filter to reduce the amount of ammonia and hydrogen sulfide that is emitted from contents in the waste collection area 8 from entering the air within the agricultural building 6. Alternatively, the cover members can be formed from a single, integrated piece of material instead of having a frame and an outer layer (not shown). For example, the cover member 10 can be formed of a single piece of molded plastic, Styrofoam, polyethylene, or other similar materials. In addition, the cover member 10 can alternatively be made of a solid material without an inner volume 27 without departing from the scope of the invention. Alternatively, still, cover member 10 can include a base 22 that extends across the bottom of the cover member to confine gases below the cover member.

The cover members 10 are introduced into the waste collection area 8 by dropping or placing the cover members into the waste material 14 within the waste collection area. Because the cover members 10 are buoyant, the cover members will float at the surface 12 of the waste material 14 with the apex 24 extending vertically out of the waste material and at least a portion of the inner volume 27 will extend above the surface to collect gaseous emissions. The cover members 10 can be weighted to ensure that the base 22 contacts the surface 12 of the waste material 14 and the upper cover portion 23 extends above the surface. Furthermore, as the number of cover members 10 introduced into the waste collection area increases, the cover members will tend to align themselves. The cover members each have a base 22 that is shaped to allow the covers members to closely align themselves to cover substantial portions if not all of the surface 12 of the waste material 14. Thus, the cover members 10 will collectively provide a cover to reduce the amount of ammonia and hydrogen sulfide that escapes from the waste collection area 8 and into the building 6.

When new animal waste is dropped, shoveled, washed or otherwise falls through the floor 9 and into the waste collection area 8, the sloped shape of the cover member 10 allows the cover member to slough off animal waste as it falls on it. Therefore, the cover members 10 will continue to float above and cover the waste material 14, even as new animal waste is added to the waste collection area 8. In one embodiment, the cover member 10 is a regular right pyramid having a base measuring about one foot by one foot and an altitude of about 2.75 inches. However, the actual dimensions of the cover member 10 can vary without departing from the scope of the invention.

FIGS. 5A, 5B, and 6 a cover member 110 in accordance with another illustrative embodiment of the current invention. Cover member 110 includes a hexagonally shaped base 122 and an upper cover portion 123 that is a right regular pyramid with six faces, each extending from a side 128 of the base. However, the vertically upper cover portion may be formed of any pyramid without departing from the scope of the invention. Other than the hexagonal base 122 and the resulting differences in the upper cover portion 123, cover member 110 can be substantially the same as cover member 10 and similar features are identified with reference numbers in the "1xx", series.

FIGS. 7A and 7B illustrate a cover member 210 in accordance with another embodiment of the current invention. Cover member 210 includes a square base 222 and an upper cover portion 223 that is a right regular pyramid with four faces, each extending from a side 228 of the base. Cover member 210 is made of a vinyl material and is inflated with air. Cover member 210, in one embodiment does not include a frame such as the frame 30 of cover member 10. However, it may include a frame without departing from the scope of the invention.

FIGS. 8A, 8B, and 9 illustrate a cover member 310 in accordance with another embodiment of the current invention. Cover member 310 includes a bottom layer 342 of material attached to the cover member to extend across the base of the frame (not shown). The bottom layer 342 of material is preferably made of geotextile material, although other materials may be used. The bottom layer 342 defines a bottom surface 329 of the cover member 310. Cover member 310 is generally hollow and has an inner volume 327 in which a filtering material 344 is located. The filtering material 344, in one embodiment, includes organic material such as wood chips or compost that can act to absorb some of the gases are emitted by animal waste material. In addition, the filtering material 344 can include other materials, such as Styrofoam beads, that improve the buoyancy of the cover member 310. With the exception of the differences described above, cover member 310 can be substantially the same as cover member 10 and similar features are identified with reference numbers in the "3xx" series.

The embodiments described above are for illustrative purposes only. The shape of the cover members can vary without departing from the scope of the invention. For example, the bases of the cover members are shaped to allow adjacent cover members to be positioned closely together to maximize coverage of the surface of the waste material. Therefore, other shapes can be used without departing from the scope of the invention. Further, while the embodiments describe the cover members including geotextile material, vinyl, and/or polyethylene, other materials can be used. For example, portions of the cover members may include a variety of different polymers.

Further still, the upper cover portion may be formed of any pyramid, regular or otherwise, or other sloping shapes including a conical shape or irregular shape that will facilitate sloughing off of falling animal waste without departing from the scope of the invention. Further still, the base and the upper cover portion of the cover member can be formed from similar or identical materials.

FIGS. 10, 11A-C, and 12 illustrate a waste collection area 408 holding waste material 414 and cover members 410 adapted to cover the waste collection area according to another embodiment of the invention. Waste collection area 408 is, in one illustrated embodiment, an open air lagoon or tank such as those found on dairy farms that includes waste material 414 such as feces or urine. Alternatively, waste collection area 408 can be a municipal lagoon including human waste or a lagoon including the waste product from a meat packing plant. The waste collection area 408 of the illustrated embodiment has a generally constant cross-sectional area at any depth from a top 413 of the waste collection area. Alternatively, the waste collection area 408 can have a generally decreasing cross-section area from the top 413 to the bottom 415 of the waste collection area. Further, while the illustrated embodiment includes a generally rectangular waste collection area 408, the waste collection area can be of any shape without departing from the scope of the invention.

Cover member 410 is a generally flat member and includes a first layer 442 of material that extends along a top surface 429 of the cover member. First layer 442 is preferably made of geotextile material. In addition, a second layer 446 of material, also preferably made of geotextile material, is positioned parallel to and extends along at least a substantial portion of the first layer 442. Cover member 410 also includes, in the illustrated embodiment, a spacer member 460. The spacer member 460 is a generally flat piece member that includes Styrofoam or other similar material formed into a pattern having a number of vacancies 462 through the spacer member from a first surface 464 to a second surface 466. While the spacer member may have any thickness 468 from the first surface 464 to the second surface 466, in one embodiment, the thickness is about three inches.

The first layer 442 is attached to the spacer member 460 along the first surface 464, using an adhesive or other known methods. The second layer 446 is attached to the second surface 466 of the spacer member, thereby enclosing the vacancies 462 in the spacer member 460 and creating a number of pouches 450 within the cover member. Alternatively, the spacer member 460 may include a plurality of pieces of material (not shown) that can be attached together to provide the pattern shown in FIG. 11B. Alternatively still, a plurality of pieces of material can be positioned along and attached to the first and second layers (not shown) to form the spacer member. In the illustrated embodiment, the pouches include a filtering material 470 within the pouches. The filtering material 470 preferably includes organic material such as wood chips and compost.

Alternatively, the first layer 442 of the cover member 410 is attached to the second layer 446 along a plurality of spaced locations to create a plurality of pouches 450 having filtering material between the first and second layers without a spacer layer (not shown). The filtering material (not shown) preferably includes organic material such as wood chips and compost. In addition, the filtering material also preferably includes a buoyant material such as Styrofoam. The second layer 446 is attached to the first layer 442 with an adhesive, stitching, a geotextile weld, or other appropriate approach.

Cover member 410 can be made of any dimension, but in one embodiment is seven feet wide and having an appropriate length to extend across the waste collection area 408. The plurality of pouches 450 can be of any size but are preferably sized to prevent the filtering material 444 from bunching up within the cover member 410. In addition, the number of pouches 450 may vary without departing from the scope of invention, including an alternative embodiment, in which the cover member 410 has have a single pouch (not shown).

Cover member 410 is introduced into waste collection area 408 by pushing or pulling it onto the surface 412 of the waste material 414. The cover member 410 is in direct contact with the waste material 414, floats on the waste material, and is supported by the surface of the waste material. As the level of the waste material 414 fluctuates, the cover member 410 can float up or down with the waste material.

In one embodiment, a single cover member 410 is not large enough to cover the entire waste collection area 408. Two or more cover members 410 are then introduced to the waste collection area 408. Cover members 410 of different sizes and shapes can be used. Prior to being introduced, the cover members 410, in one embodiment, are attached to each other (not shown) by stitching, geotextile welding, use of an adhesive, or other known attachment structures. The plurality of cover members 410 are then positioned over the waste material 414 so that when introduced to the waste collection area, the cover members extend over most or all of the surface 412 of the waste material at the largest cross-sectional area within the waste collection area 408. Cover members 410 of different sizes and shapes can be used together to cover just the waste material 414 within the waste collection area 408 without departing from the scope of the invention.

As the depth of the surface 412 varies within the collection area 408, the cover member 410 or plurality of cover members will, in one embodiment, rise or fall on the surface of the waste material 414. The area of the surface 412 may vary at different depths within the waste collection area. When the surface 412 has a smaller area than the cover member 410, the cover member may extend over the surface of the waste material 414.

Figure 13A:
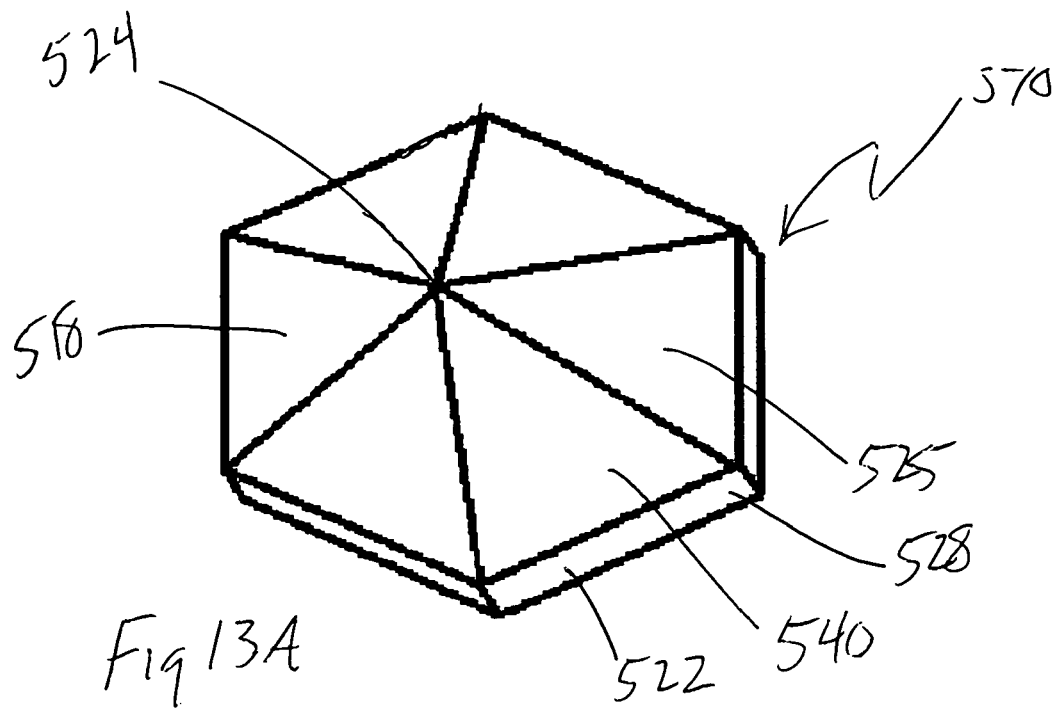
FIGS. 13A and 13B are isometric views of top and bottom views of a cover member for the waste collection area of FIG. 10 having a pyramid shape according to yet another embodiment of the invention.
Figure 13B:
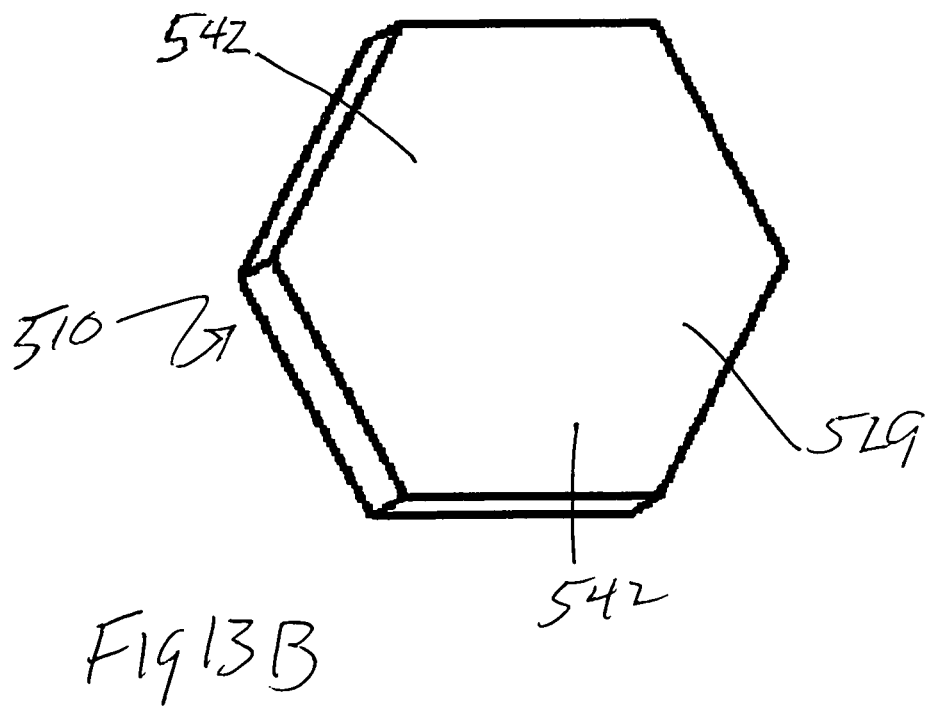

FIGS. 13A and 13B illustrate a cover member 510 adapted for use in a waste collection area 408 as is shown in FIG. 10 according to yet another embodiment of the invention. Cover member 510 is, in the illustrated embodiment, a hexagonal pyramid shaped cover having lateral faces 518 extending from a base 522 that floats over a portion of the waste material 414 in collection area 408 so that the apex 524 extends above the surface 412 of the waste material. In one embodiment, a plurality of cover members 510 are positioned on the surface 412 of the waste material 414. The bases 522 of the plurality of cover members 510 are shaped, as in the illustrated embodiment, to be positioned closely together to allow the cover members to cover a substantial portion, if not all, of the waste material 414 within the collection area 408.

In one embodiment, the cover member 510 is hollow and includes a frame (not shown) that defines the shape of the cover member and an outer layer 540 of material, preferably a geotextile material, that is attached to the frame and forms the faces 518 of the cover member. The frame can be formed from material such as polyethylene. The frame defines an inner volume (not shown), which holds filter material (not shown). The filter material includes, in one embodiment organic, materials such as wood chips and compost. Alternatively, the filler material also includes buoyant material. Alternatively still, the filler material includes material to provide added weight to ensure that the cover member 510 floats in the waste collection area 408 with an orientation where the apex 524 extends vertically from the surface 412 of the waste material 414.

In yet another embodiment, the cover member 510 is a single piece of buoyant material such as a polymer member that defines the shape of the cover member and forms the outer surface 540 of the cover member. The single piece cover member can also include an inner volume with filter material such as the type described above.

In one embodiment, the cover member 510 has a base 522 with sides that measure about 7 feet and an altitude of about 2.5 feet, although the cover member may vary in size. Similarly, the cover member 510 may have the shape of any pyramid or other similar shapes without departing from the scope of the invention. With the exception of differences described above primarily related to the size of the cover member, cover member 510 is similar in construction to the cover member 310 and similar features are identified in the "5xx" series. Likewise, a plurality of cover members 510 may be introduced into the waste collection area 408 to provide a cover for the waste material 414.

The current invention has a number of advantages. Experimentation has shown that the use of cover elements within the waste collection area of an agricultural building reduced the ammonia levels within the agricultural building by up to 80% to 90% after twenty-four hours. Not only does the reduction of ammonia within the building lead to lower emissions out of the agricultural building itself, but the lower levels of ammonia within the building result in less usage of ventilation fans that are used to evacuate ammonia from the building, leading to lower electricity costs associated with the operation of the building. In addition, the use of a cover on an open air lagoon that includes both the ability to float on the surface of the waste material and filtering material leads to reduced emissions from lagoons, thereby providing assistance to reach the regulatory and aesthetic goals of acceptable levels of emissions.

Those skilled in the art will appreciate that modifications can be made to the illustrative embodiments without departing from the scope of the invention.

What is claimed is:

1. An animal waste collection area with liquid animal waste collected therein and having a plurality of buoyant cover members floating on the surface of the animal waste, each cover member adapted to confine gaseous emissions from animal waste in the waste collection area and comprising a waste-contacting base contacting and floating on the surface of the animal waste and a sloping cover to slough animal waste falling on the cover member into the waste collection area.

2. The waste collection area of claim 1, wherein at least one surface of the cover generally slopes from the base toward an apex of the cover.

3. The waste collection area of claim 2, wherein the cover has a generally pyramid shape.

4. The waste collection area of claim 1, further comprising a frame to define a shape of the cover member.

5. The waste collection area of claim 4, wherein the frame includes a buoyant material.

6. The waste collection area of claim 1, further comprising a first layer of material positioned along the cover to provide an outer surface of the cover.

7. The waste collection area of claim 6, wherein the first layer of material includes geotextile material.

8. The waste collection area of claim 6, further comprising a second layer of material positioned along a bottom surface of the base to enclose an inner volume of the cover member.

9. The waste collection area of claim 8, further comprising filtering material located within the inner volume of the cover member.

10. The waste collection area of claim 9, wherein the filtering material comprises an organic material.

11. The waste collection area of claim 1, further comprising an aperture formed through the cover.

12. The waste collection area of claim 1, wherein the base is shaped for allowing the cover member to be closely aligned with one or more other cover members.

13. The animal waste collection area of claim 1, wherein at least one cover member is attached to another cover member.

14. The animal waste collection area of claim 1, wherein the waste collection area is located beneath an agricultural building.

15. An animal waste collection area for collecting animal waste comprising one or more cover members comprising:
   a first layer of porous geotextile material;
   a second layer or porous geotextile material;
   an attachment member for securing the first layer and the second layer to form a plurality of pouches between the first layer and the second layer; and
   organic filter material located in the pouches.

* * * * *

UNITED STATES PATENT AND TRADEMARK OFFICE
CERTIFICATE OF CORRECTION

| | | |
|---|---|---|
| PATENT NO. | : 7,491,265 B1 | Page 1 of 1 |
| APPLICATION NO. | : 11/155669 | |
| DATED | : February 17, 2009 | |
| INVENTOR(S) | : Dennis J. Johnson et al. | |

It is certified that error appears in the above-identified patent and that said Letters Patent is hereby corrected as shown below:

Column 8, line 49 [claim 15] delete "or" and insert therefor --of--

Signed and Sealed this

Twenty-sixth Day of May, 2009

JOHN DOLL
*Acting Director of the United States Patent and Trademark Office*